Jan. 2, 1962 L. A. LAMBOROT Plant Pat. 2,119
CHRYSANTHEMUM PLANT
Filed March 30, 1960
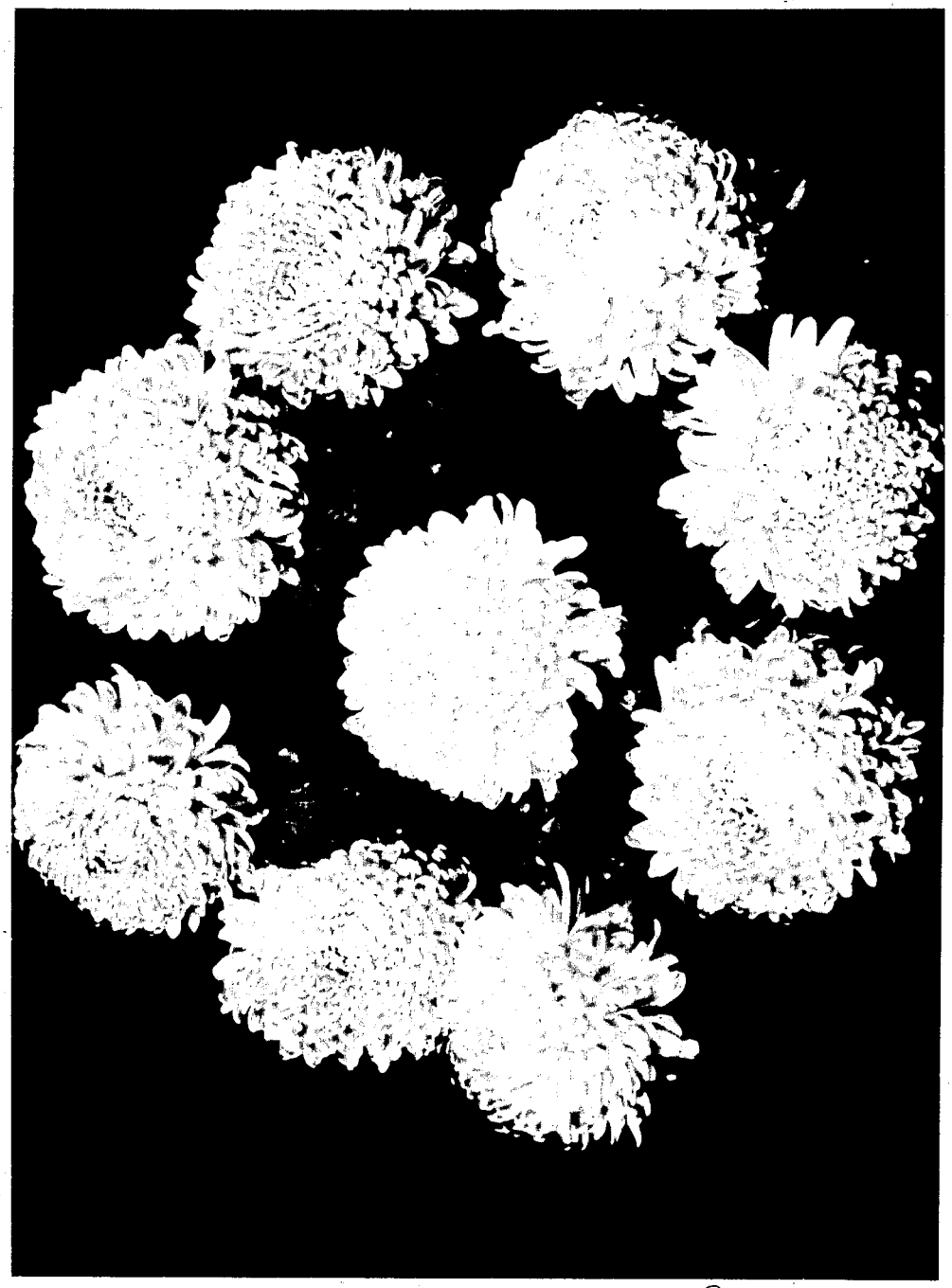
Inventor
L. A. Lamborot
by Robb & Robb
Attorneys United States Patent Office Plant Pat. 2,119
Patented Jan. 2, 1962

2,119
CHRYSANTHEMUM PLANT

Lazare Antoine Lamborot, Montceau les Mines, France, assignor to George J. Ball, Inc., West Chicago, Ill., a corporation of Illinois Filed Mar. 30, 1960, Ser. No. 18,794
1 Claim. (Cl. 47—60)

My present invention comprises a new and distinct variety of chrysanthemum plant, and which is a seedling produced as a result of crossing the variety No. 54–2, an unpatented variety of my own production, with another variety of my own production which I have designated as No. 55–53, and likewise unpatented.

The object of this invention has been to produce a new variety of chrysanthemum plant of the *morifolium* type, which is a substantial improvement in the general class of commercial pink varieties, some of the features of improvement being the greatly increased size of bloom, the blooms on any single plant tending to open more nearly at the same time, such blooms being found on shorter stems, with more pleasant color, the fading of such color being more uniform and gradual.

My new variety is one of many different varieties which have been developed by me in a continuous program of extensive range, involving careful selection and cross-breeding of various chrysanthemum varieties to produce the shorter more compact habit of growth than the known varieties previously existent.

The result of the specific hybridization mentioned heretofore, has been to produce my present new and distinct variety of chrysanthemum plant, characterized by the very large blooms of a color between strong purplish pink and deep purplish pink, the very double arrangement of its petals, the shorter length of stems, more compact habit, and profuse, though intermittent and mid-fall blooming period.

More specifically, the blooms of my new variety, have a general tonality from a distance between strong purplish pink and deep purplish pink color (Nickerson Color Fan, published by Munsell Color Company).

As grown in the vicinity of Montceau les Mines, France, under uniform culture conditions, my new variety has continuously grown in more uniform compact bushes, with abundant large foliage and a virtual immunity to disease.

In the pot chrysanthemum trade in the United States, there are several known varieties of pinks, the three most popular and generally accepted, probably being those identified as "Criterion," "Blue Ribbon" and "Queen of Pinks," all unpatented varieties.

My new variety is an improvement over the variety "Criterion" because the flower of my variety will in many cases be as much as twice as large as the said variety, when grown under favorable conditions, but in most instances, substantially larger at least. Further, whereas "Criterion" is tall and thus not so desirable for pot growing, my new variety is shorter and more compact. The color of my new variety is also more pleasant as contrasted with the somewhat harsh impression created by "Criterion."

My new variety is a definite improvement over "Blue Ribbon" because the latter is substantially smaller, as much as sixty to seventy percent in many instances. Further "Blue Ribbon" tends to fade radically, whereas my new variety fades much more uniformly and slowly.

Compared to "Queen of Pinks" my new variety produces blooms often twice as large. In addition "Queen of Pinks" has the serious fault of opening unevenly, that is some blooms open as much as a week or ten days before others, whereas the blooms of my new variety open much more nearly at the same time and thus provide a pleasing display for pot use.

I believe the foregoing generally points out some of the important, noticeable differences which exist between some of the more prominent known varieties and my improved new variety, which makes the latter more attractive and commercially appealing.

Under the conditions of culture which have been provided in the vicinity of Montceau les Mines, France, plants of my new variety have exhibited vigorous growth, with blooms on somewhat shorter stems than prior plants the blooms themselves being much larger and the stems providing more compact, showy appearance.

My new variety has been asexually reproduced by cuttings in the vicinity of Montceau les Mines, France, and found to retain its distinctive characteristics through such reproduction. The accompanying drawing forming a part hereof shows a typical plant of my new variety of chrysanthemum.

The following is a detailed description of my new variety of chrysanthemum plant, the color references being to the Nickerson Color Fan published by the Munsell Color Company:

*Description*

Parentage: Seedling.
*Seed parent.*—54–2.
*Pollen parent.*—55–53.
Classification: Botanic—*Chrysanthemum morifolium.*

*Flower*

Blooming habit: Blooms profusely though intermittently at mid-fall.

Bud:
*Size.*—large.
*Form.*—Short with flat top. Not affected by hot or wet weather.
*Color.*—When sepals first divide—7.5RP 5/12 strong purplish red with yellow overtones. When petals begin to unfurl— 7.5RP 6/12, deep purplish pink. When half blown, inside of petals—between 7.5RP 7/10, strong purplish pink and 7.5RP 6/12 deep purplish pink. When half blown, reverse of petals—7.5RP 7/10 strong purplish pink.
*Sepals.*—Smooth edge.
*Calyx.*—Shape—funnel. Size—small. Aspect—mossy. Odor when rubbed—typical chrysanthemum odor.
*Peduncle.*—Aspect—rough. Color—medium green. Strength—stiff. Bud opens well and is not affected by adverse conditions.

Bloom:
*Size.*—Very large. Average size when fully expanded 5½ inches.
*Borne.*—In clusters and flat unless disbudded.
*Stems.*—Short and strong.
*Form.*—When first opened—high center. Permanence—retains its form to the end. Fashioned like a show dahlia.
*Petalage.*—Very double. Petals too numerous to count.
*Color.*—Center of flower—7.5RP 5/12, strong purplish red washed with 5Y 8/12 vivid yellow. Outer petals—between 7.5RP 7/10, strong purplish pink and 7.5RP 6/12, deep purplish pink. Base of petals (singlet)—7.5RP 5/12, strong purplish red. Inside of petals—between 7.5RP 6/12, deep purplish pink and 7.5RP 5/12, strong purplish red. Reverse of petals—7.5RP 7/10, strong purplish pink. General tonality from a distance—between 7.5RP 7/10, strong purplish pink and 7.5RP 6/12, deep purplish pink.

*Discoloration.*—General tonality at end of: first week—between 7.5RP 5/12, strong purplish red and 7.5RP 6/12, deep purplish pink; second week—7.5RP 6/12, deep purplish pink; third week—between 7.5RP 6/12, deep purplish pink and 7.5RP 7/10 strong purplish pink.

Petals:

*Texture.*—Thick. Not affected by wet or hot weather.

*Appearance.*—Inside—satiny. Outside—satiny.

*Form.*—Oval.

*Arrangement.*—Imbricated.

*Petaloids in center.*—Many.

*Persistance.*—Hang on and dry.

*Fragrance.*—Normal chrysanthemum odor.

*Lastingness.*—On the plant—very long. As cut flower—very long.

Genital organs:

*Stamens, anthers.*—Small. Color—yellow. Arrangement—regular around styles.

*Stamens, filaments.*—Short. Color—lemon yellow.

*Pollen.*—Lemon yellow.

*Styles.*—Columnar.

*Stigmas.*—Color—yellow.

*Ovaries.*—All enclosed in calyx.

Fruit: Variety is sterile with its own pollen.

*Form.*—Seeds protruding.

*Aspect.*—Rough.

*Color at maturity.*—Russet brown.

*Sepals.*—Caducous.

*Plant*

Form: Bush.

Growth: Compact.

Foliage:

*Leaflets.*—One (alternate).

*Size.*—Large.

*Quantity.*—Abundant.

*Shape.*—Lanceolate.

*Texture.*—Smooth.

*Ribs and veins.*—Ordinary.

*Edge.*—Undulated.

*Serrations.*—Single.

*Leaf stem.*—Color—green. Underside—rough.

*Stipules.*—Medium.

*Disease resistance.*—Immune to disease.

Wood (new):

*Color.*—Light green.

*Bark.*—Smooth.

Wood (old):

*Color.*—Green.

*Bark.*—Rough.

I claim:

A new and distinct variety of chrysanthemum plant substantially as herein disclosed, characterized as to novelty by the very large blooms of a color between strong purplish pink and a deep purplish pink, the very double arrangement of its petals, the shorter length of stem, more compact habit, more uniform fading of the blooms, and the more nearly simultaneous opening and profuse quantity of blooms.

No references cited.